US005548653A

United States Patent [19]

Pla et al.

[11] Patent Number: 5,548,653

[45] Date of Patent: Aug. 20, 1996

[54] ACTIVE CONTROL OF NOISE AND VIBRATIONS IN MAGNETIC RESONANCE IMAGING SYSTEMS USING VIBRATIONAL INPUTS

[75] Inventors: Frederic C. Pla, Schenectady; Robert A. Hedeen, Clifton Park; Imdad Imam, Schenectady, all of N.Y.

[73] Assignee: General Electric Company, Schenectady, N.Y.

[21] Appl. No.: 110,176

[22] Filed: Aug. 20, 1993

Related U.S. Application Data

[63] Continuation-in-part of Ser. No. 834,957, Feb. 14, 1992, abandoned.

[51] Int. Cl.[6] .......... A61F 11/06

[52] U.S. Cl. .......... 381/71; 128/653.2; 128/653.5

[58] Field of Search .......... 381/71, 94; 128/653.2, 128/653.5

[56] References Cited

U.S. PATENT DOCUMENTS

| | | | |
|---|---|---|---|
| 4,473,906 | 9/1984 | Warnaka et al. | 381/71 |
| 5,146,505 | 9/1992 | Pfaff et al. | 381/71 |
| 5,170,433 | 12/1992 | Elliott | 381/71 |
| 5,221,185 | 6/1993 | Pla et al. | 381/71 |
| 5,237,618 | 8/1993 | Bethel | 381/71 |
| 5,313,945 | 5/1994 | Friedlander | 381/71 |
| 5,370,340 | 12/1994 | Pla | 381/71 |

*Primary Examiner*—Curtis Kuntz
*Assistant Examiner*—Ping W. Lee
*Attorney, Agent, or Firm*—Paul R. Webb, II

[57] ABSTRACT

An active noise and vibration control system which minimizes noise output by creating a secondary, cancelling noise and/or vibration field using vibrational inputs. The system includes one or more piezoceramic actuators mounted to the inner surface of a magnetic resonance imaging device. The actuators can be either mounted directly to the device or to one or more noise cancelling members which are resiliently mounted to the device. Transducers are also provided for sensing the noise or vibrations generated by the device and producing an error signal corresponding to the level of noise or vibrations sensed. A controller sends a control signal to the actuators in response to the error signal, thereby causing the actuators to vibrate and generate a noise or vibration field which minimizes the total noise emanating from the device. Alternatively, the system can use noise and vibration feedback simultaneously.

20 Claims, 3 Drawing Sheets

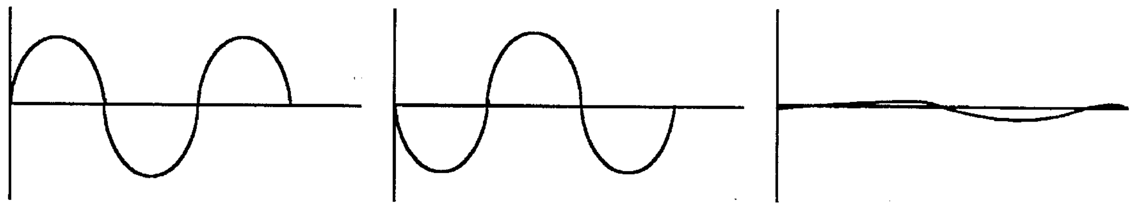
*fig. 1a* *fig. 1b* *fig. 1c*
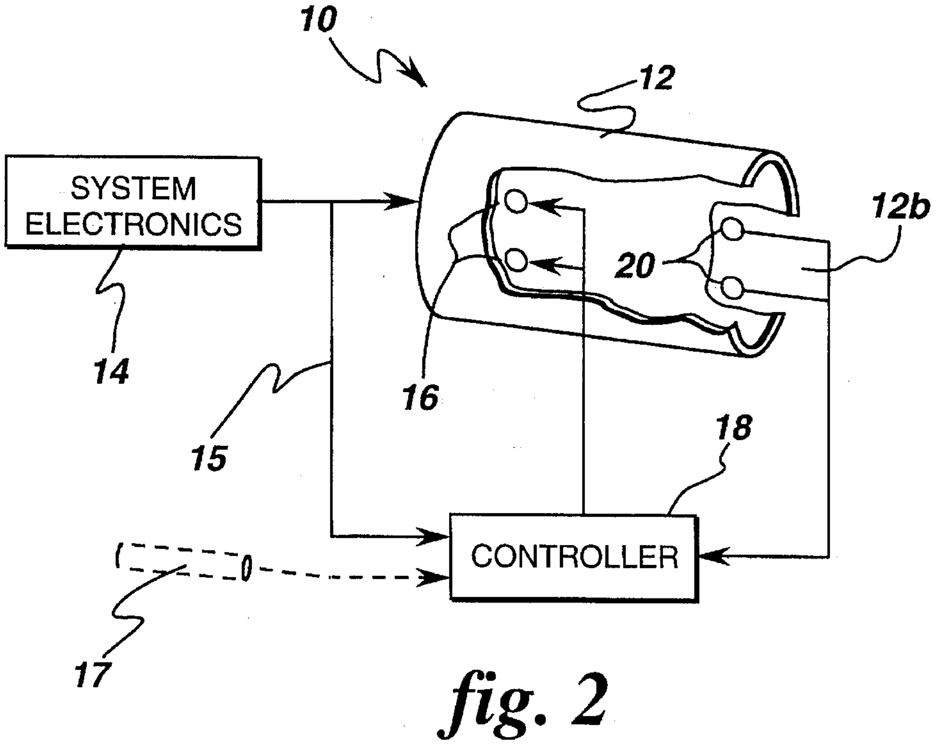
*fig. 2*

ACTIVE CONTROL OF NOISE AND VIBRATIONS IN MAGNETIC RESONANCE IMAGING SYSTEMS USING VIBRATIONAL INPUTS

CROSS REFERENCES TO RELATED APPLICATIONS

This application is a Continuation-in-part of application Ser. No. 07/834,957, filed Feb. 14, 1992, now abandoned. This application is also related to application entitled "Active Control of Aircraft Engine Noise Using Vibrational Inputs" Ser. No. 08/051 810, filed Apr. 21, 1993, now U.S. Pat. No. 5,370,340 which is a File Wrapper Continuation of application Ser. No. 07/787,471, filed Nov. 4, 1991, and now abandoned. All of these related applications are assigned to the same assignee as the present invention.

BACKGROUND OF THE INVENTION

This invention relates generally to magnetic resonance imaging (MRI) systems and more particularly concerns minimizing the noise and/or vibrations generated by an MRI system using secondary vibrational inputs.

MRI systems require a uniform magnetic field and radio frequency radiation to cause magnetic resonance in the atomic nuclei of the subject being imaged. The magnetic resonance of the nuclei provides information from which an image of the portion of the subject containing these nuclei may be constructed. The magnetic field, which must be highly homogeneous, can be generated by a large permanent or superconducting magnet. The RF radiation is generated by an RF coil situated within the magnetic field. Magnetic field gradient coils are used to encode spatial information into the image signal. Typically, these elements are arranged so as to be contained within a structure having a cylindrical bore with a diameter large enough that the subject being imaged can be placed within the cylinder. A more complete discussion of MR imaging may be found in U.S. Pat. No. 4,471,306 assigned to the same assignee as the present invention.

Magnetic resonance imaging is now a widely accepted medical diagnostic procedure and its use is becoming increasingly popular. However, the acoustic noise levels generated by current MRI systems approach 100 decibels. These high noise levels can cause a substantial degree of patient discomfort and often require a test to be aborted prior to completion. MRI technology is not available to some patients only because they are unable to cope with the MRI environment. Noise is also a major concern for staff members operating the devices.

SUMMARY OF THE INVENTION

Accordingly, it is an object of the present invention to reduce the acoustic noise levels generated by MRI systems.

More specifically, it is an object of the present invention to reduce MRI system noise by creating a secondary noise and/or vibration field which cancels the primary noise field.

In addition, it is an object of the present invention to control vibrations in the MRI system in order to maintain good image quality.

These and other objects are accomplished in the present invention by coupling one or more piezoceramic actuators to the MRI system. The actuators can be either mounted directly to the system or to one or more noise cancelling members which are resiliently mounted to the MRI device.

Transducers are also provided for sensing either the noise generated by the MRI system or the vibrations in the system. The transducers produce error signals corresponding to the level of noise or vibrations sensed. A controller is included and has inputs connected to the transducers and outputs connected to the actuators. A reference signal representing the primary noise field is also fed to the controller. The controller is responsive to the error and reference signals to determine a control signal which is sent to the actuators, thereby causing the actuators to vibrate and generate a noise or vibration field which minimizes the total noise emanating from the MRI system. Alternatively, both noise and vibration transducers can be used together, with the controller being responsive to both error signals in determining the control signal.

In another embodiment, both noise and vibration feedback are used but independently of one another. Noise transducers provide noise error signals to a first controller, and vibration transducers provide vibration error signals to a second controller. The first controller sends a control signal to a first set of actuators resiliently mounted to the MRI device, while the second controller sends a control signal to a second set of actuators directly mounted to the device.

Other objects and advantages of the present invention will become apparent upon reading the following detailed description and the appended claims and upon reference to the accompanying drawings.

DESCRIPTION OF THE DRAWINGS

The subject matter which is regarded as the invention is particularly pointed out and distinctly claimed in the concluding portion of the specification. The invention, however, may be best understood by reference to the following description taken in conjunction with the accompanying drawing figures in which:

FIGS. 1A–1C show a typical acoustic wave generated by a primary noise field, a secondary noise field, and the combined noise field, respectively;

FIG. 2 is a schematic representation of a first embodiment of the present invention;

DETAILED DESCRIPTION OF THE INVENTION

Figure 3:
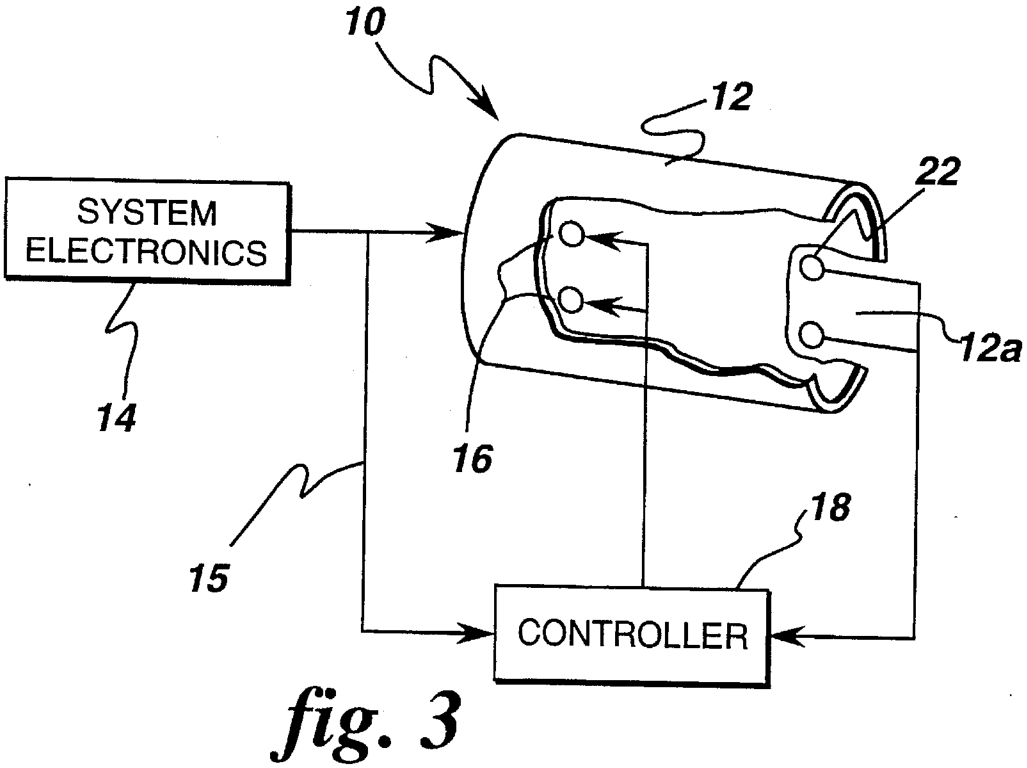
FIG. 3 is a schematic representation of a second embodiment of the present invention.

The underlying principle of the present invention is explained with reference to FIGS. 1A–1C. FIG. 1A shows a sample acoustic wave which may be generated during operation of an MRI system. This is referred to as the primary noise field. FIG. 1B shows an acoustic wave purposely generated by a secondary or cancelling noise source. As can be seen in these figures, the secondary wave is out-of-phase with the primary wave. The effect of the two waves being out-of-phase is that they cancel one another out, thus eliminating noise. This can be seen in FIG. 1C where the composite wave has virtually zero amplitude.

Turning to FIG. 2, which is a simplified block diagram of the present invention, an MRI system 10 is shown. Since the MRI system in and of itself does not form a part of the present invention, it is simply shown as a cylindrical structure 12. It should be understood that the cylinder 12 includes the magnet, RF coil, gradient coils and other hardware of a conventional MRI system. Also included are MRI system electronics 14 that generate RF pulse signals which are applied to the RF coil in the cylindrical structure 12. The RF pulse signals have the modulation required to excite resonance in the subject being studied. The system electronics 14 also generate gradient pulse signals which energize the gradient coils in the cylinder 12. Both the RF pulse signals and the gradient pulse signals are represented in the Figures by the signal 15. The system electronics 14 are conventional and need not be further described. Reference is made to the above-mentioned U.S. Pat. No. 4,471,306 for a more detailed description of conventional MRI system electronics.

In a first embodiment of the present invention, vibrational input sources are provided to generate a secondary noise field which serves to cancel the primary field. FIG. 2 shows the cylinder 12 partially cut away to reveal a plurality of vibrational actuators 16 attached to an inner surface thereof. The actuators 16 provide the necessary vibrational input to "shake" the structure they are attached to, thereby creating the secondary noise field. The actuators can be either directly attached to the cylinder 12 or indirectly coupled via a mounting arrangement which will be described below. The actuators 16 are controlled by an electronic controller 18 connected to each of the actuators. The controller 18 receives input from a plurality of feedback sensors 20 disposed on the cylinder 12. In the embodiment of FIG. 2, noise transducers are provided as the feedback sensors. The noise transducers 20 sense noise generated by the MRI system and produce an error signal corresponding to the level of noise sensed. The transducers 20 can be microphones, piezoelectric films, piezoelectric transducers or any other type of device capable of sensing noise and producing an output thereof. The noise transducers 20 are generally located wherever noise needs to be eliminated. Preferably, a number of transducers 20 are arranged in the cylinder 12 so as to be in proximity to a patient's ears when the patient is placed in the device for a test.

The controller 18 also receives an input of a reference signal representing the primary noise field. The reference signal may be derived from any source as long as there is a well correlated transfer function between the reference signal and the primary noise field. For instance, the reference signal may be derived from the gradient pulse signals or even from the RF pulse signals (both denoted in the Figures by reference numeral 15). The gradient pulse signals are a particularly good source for the reference signal because they are primarily responsible, in their amplified form, for the original source of the MRI noise. Alternatively, the reference signal may be derived from a microphone 17 positioned to detect the primary field but not the secondary field. (Being an alternative, the microphone 17 is schematically shown in dotted lines in FIG. 2.) For example, the microphone 17 could be placed near the opening of the bore of the cylindrical structure 12 or between the RF coil and the gradient coils of the MRI device. The reference signal must not contain crosstalk from the secondary noise field.

Thus, the input of the reference signal provides primary field frequency information to the controller 18, while the noise transducers 20 provide performance feedback information to the controller 18. In response to the inputs from the transducers 20 and the reference signal, the controller 18 determines an appropriate control signal which is sent to each of the actuators 16. The control signal causes the actuators 16 to vibrate with the frequency and amplitude needed to shake their supporting structure and create the proper secondary noise field for minimizing total noise.

The controller 18 can be implemented using one of a variety of standard control schemes known in the art. One preferred scheme uses a multi-input, multi-output (MI/MO) adaptive filtering approach based on the MI/MO Filtered-X LMS algorithm. Such an algorithm is described in the article "A Multiple Error LMS Algorithm and its Application to the Active Control of Sound and Vibration," *IEEE Transactions on Acoustic Speech and Signal Processing*, Vol. ASSP-35, No. 10, October, 1987, by Stephen Elliott et al. In such a control scheme, the control signals which are sent to the actuators 16 are adjusted in real time to minimize noise at the noise transducers 20. The controller 18 can react nearly instantly to frequency modulations in the reference signal. Moreover, due to its adaptive nature, the controller is self-configuring and can self-adapt to changes in the system such as actuator or transducer failure.

The actuators 16 are preferably made of a piezoceramic material, typically in the form of a thin sheet. Piezoceramic actuators are preferred because, unlike electrodynamic shakers or traditional, voice coil loudspeakers, piezoceramic material is non-magnetic. Thus, piezoceramic actuators will not interfere with the magnetic field of the MRI system. Piezoceramic actuators are also much lighter than traditional loudspeakers, are low power consuming devices which can be distributed over a large area and are designed to ensure good impedance matching with the acoustic field inside the MRI system. Furthermore, the number of sources needed for active noise control is less when using vibrational inputs than when using acoustic sources such as traditional loudspeakers. This is because the sound field obtained using structure-borne excitation (vibrational sources) more closely approximates the required cancelling field than a sound field obtained using nonstructure-borne excitation (acoustic sources).

The piezoelectric properties of each actuator 16 are such that, when excited, it exerts an oscillating force on the plane of the structure to which the actuator is attached. Structure-borne noise is then generated when in-plane vibrations change the shape of the cylindrical structure and produce bending motions. The size of the actuators 16 depends on the acoustic power required to produce the secondary sound field. The number and placement of the actuators depends mainly on the modal order of the primary noise field to be cancelled. For instance, in the case of primary noise being generated by a distributed source, it is best to provide a distributed secondary source to generate the secondary noise field. One solution is a modal actuation approach using distributed actuators shaped so that they only excite certain modes. Use of distributed actuators also tends to minimize modal spillover problems.

For best results, the actuators should be arranged to closely resemble the excitation mechanism of the primary noise field. In other words, it is best to cancel the primary noise of the MRI system at its source. For the structure-borne nature of MRI noise, this means cancelling the primary vibration field in order to reduce the noise. This could be accomplished in the special circumstance where the coupling between the vibration and acoustic fields of the MRI system can be determined. FIG. 3 shows a second embodiment of the present invention in which MRI noise is reduced through such vibration cancellation. The FIG. 3 embodiment is structurally identical to the FIG. 2 embodiment except that the noise transducers 20 are replaced with vibration transducers 22. The vibration transducers 22 are devices such as accelerometers that sense the vibration modes which radiate the most noise and output error signals corresponding to the sensed vibrations. The error signals and a reference signal are fed to the controller 18 which in turn sends an appropriate control signal to the actuators 16 to cancel the detrimental vibration modes. The reference signal can be derived from either the gradient pulse signals or the RF pulse signal (represented by signal 15 in FIG. 3), or the reference signal can be derived from a microphone positioned in or near to the MRI system 10. In this embodiment, the actuators 16 are preferably mounted on the gradient coils 12*a* (see FIG. 3) because the energization of the gradient coils is a primary source of the MRI noise. The RF coil 12*b* (see FIG. 2) is another location on which the actuators 16 could be mounted.

Figure 4A:
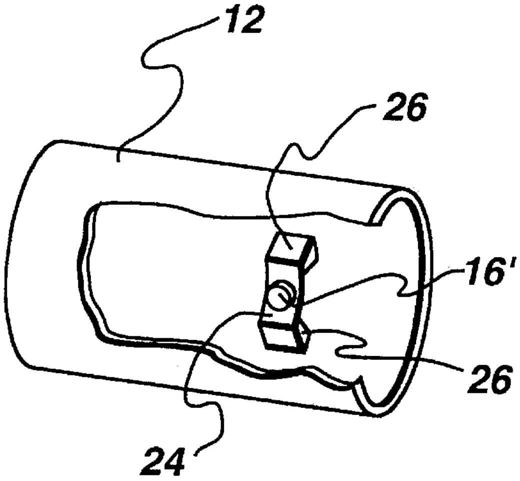
FIG. 4A is a partially cut-away perspective view of the present invention showing a resilient mounting arrangement for a vibrational actuator.
Figure 4B:
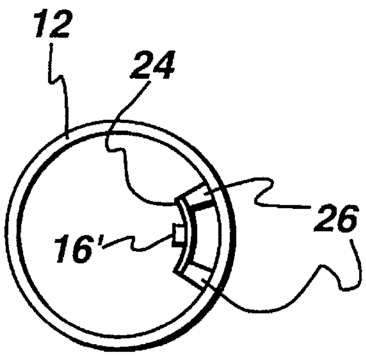
FIG. 4B is an end view of the present invention showing the resilient mounting arrangement.

The noise cancellation techniques of the first embodiment may increase vibration levels in the MRI system structure due to the secondary vibrational inputs and modal spillover. If increased structural vibrations adversely affect image quality, the actuators can be indirectly mounted via a resilient mounting arrangement, thereby decoupling the secondary vibrational inputs from the MRI system structure. FIGS. 4A and 4B show such a mounting arrangement in detail. A thin, arcuate noise cancelling member 24 is concentrically mounted to the inner surface of the cylinder 12. The noise cancelling member 24 is preferably mounted to the cylinder 12 by means of two fasteners (not shown) and two resilient mounting members 26 at both ends of the arcuate member 24. One or more actuators 16' are then mounted to the noise cancelling member 24. Thus, the actuators shake the noise cancelling member 24 in order to radiate secondary noise towards the patient. Although only one noise cancelling member 24 is shown, any number as needed could be included. The resilient mounting members 26 are preferably elastic blocks disposed between the cylinder 12 and the opposing ends of the noise cancelling member 24. The resilient mounting members 26 prevent the noise generating vibrations of the actuators from propagating to cylinder 12. This arrangement thus limits image distortion due to the noise cancelling vibrations.

Figure 5:
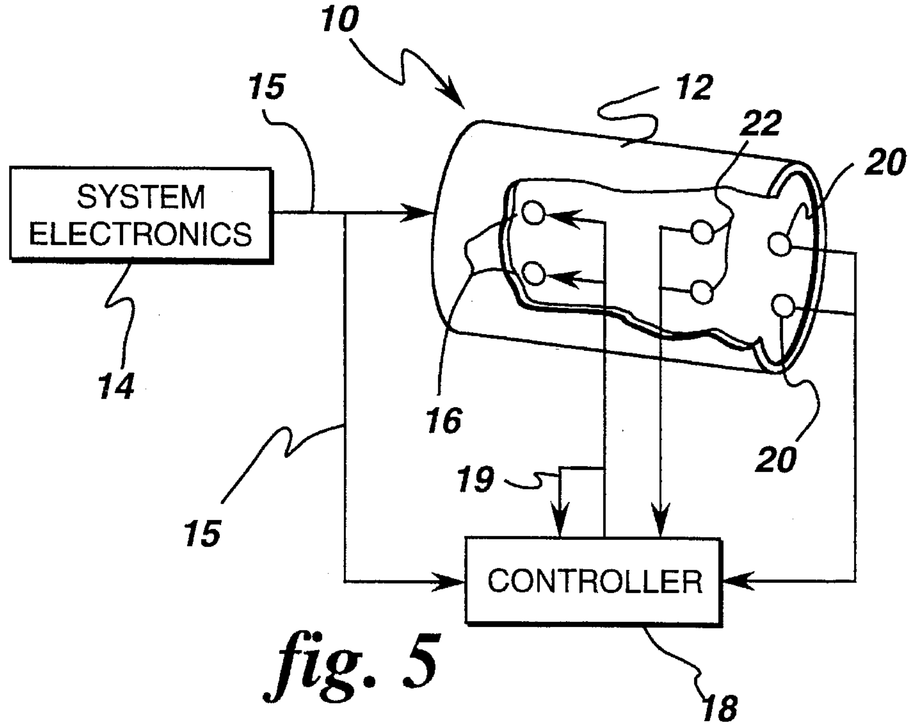
FIG. 5 is a schematic representation of a third embodiment of the present invention.

FIG. 5 shows another way to protect image quality from secondary vibrations which includes adding a vibration feedback term and an "effort" term to the noise feedback signal fed to the controller. The system of FIG. 5 is the same as the system of FIG. 2 except that one or more secondary feedback sensors 22 are provided in addition to the noise transducers 20. The secondary feedback sensors are vibration transducers such as accelerometers. The vibration transducers 22 sense vibrations generated in the MRI system and produce an error signal corresponding to the sensed vibrations. The vibration error signal is fed to the controller 18 in addition to the noise error signal from the noise transducers 20 and a reference signal which can be derived from either the gradient pulse signals or the RF pulse signal (represented by signal 15 in FIG. 5), or from a microphone positioned in or near to the MRI system 10. The vibration feedback allows the controller 18 to minimize vibrations at the vibration transducers 22, thereby minimizing primary vibrations, excessive secondary vibrations, and modal spillover problems to preserve image quality.

The "effort" term is a signal 19 proportional to the control signal emitted from the controller 18 to the actuators 16 that is added to the noise and vibration feedback signals. The "effort" term ensures that minimum power, and thus minimum resultant vibrations, is used by the actuators in reducing noise. Furthermore, when multiple actuators are used, the "effort" term prevents the actuators from generating excessive vibrations as a result of the actuators trying to cancel vibrations from other actuators.

When combining vibration cancellation with noise cancellation, a compromise has to be made between the two techniques, because a reduction in noise is usually accompanied by an increase in vibration. By carefully analyzing the noise and vibration fields in the system, the best location, size and number of actuators and sensors, as well as the best control parameters, can usually be determined to strike an optimum compromise between noise and vibration cancellation.

Figure 6:
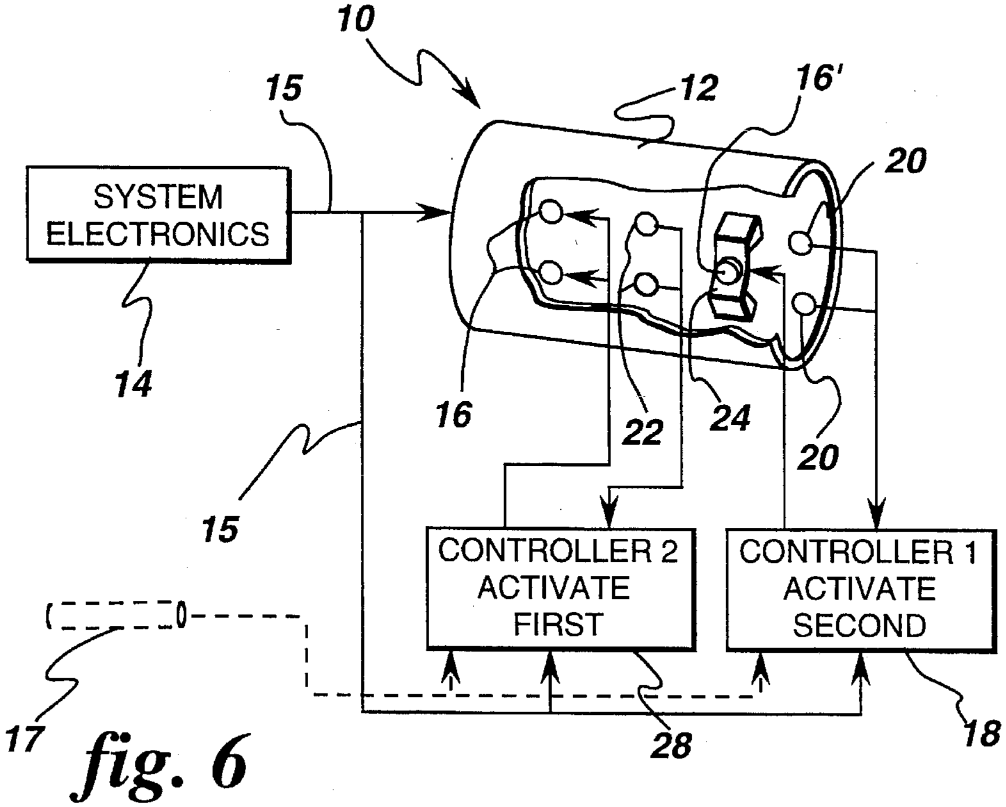
FIG. 6 is a schematic representation of a fourth embodiment of the present invention.

FIG. 6 shows an embodiment for use when a satisfactory compromise between noise and vibration cancellation cannot be found. This approach uses the resilient mounting arrangement discussed above to decouple noise cancellation from vibration cancellation. As seen in FIG. 6, noise transducers 20 mounted to the MRI structure 12 provide noise error signals to a first controller 18, and vibration transducers 22 provide vibration error signals to a second controller 28. Both the first and second controllers receive an input of a reference signal representing the primary noise field. As before, the reference signal can be derived from either the gradient pulse signals or the RF pulse signal (represented by signal 15 in FIG. 6), or the reference signal can be derived from a microphone positioned in or near to the MRI structure 12. The system also has a number of actuators 16 mounted directly to the MRI cylindrical structure 12 (particularly to the gradient coils and/or the RF coil) and at least one actuator 16' mounted via a resilient mounting arrangement which is equivalent to the arrangement of FIGS. 4A and 4B. The number and placement of these actuators depends mainly on the modal order of the primary noise field to be cancelled.

The first controller 18 determines an appropriate control signal in response to the inputs from the noise transducers 20 and the reference signal. This control signal is sent to the actuator 16'. As described above, the actuator 16' is resiliently mounted to the MRI structure 12 via a noise cancelling member 24 and two resilient mounting members 26. The control signal from the first controller 18 causes the actuator 16' to shake the noise cancelling member 24 to create a secondary noise field for minimizing total noise. The resilient mounting prevents generation of secondary vibrations in the MRI structure 12. In response to the inputs from the vibration transducers 22 and the reference signal, the second controller 28 determines an appropriate control signal which is sent to the actuators 16. The control signal causes the actuators 16 to vibrate with the frequency and amplitude needed to shake their supporting structure and create a secondary vibration field that will minimize overall vibrations in the MRI structure.

Thus, it can be seen that the embodiment of FIG. 6 has a noise cancelling control loop based around the first controller 18 which reduces noise without creating secondary vibrations and a vibration cancelling control loop based around the second controller 28 which minimizes structural vibrations independently of the noise control. Since the vibration field affects the overall noise field, the second controller 28 should be activated first. Once the vibration control loop has reached a steady state, the first controller 18 can be activated with no effect on vibration cancellation because the secondary noise field created by the noise control loop does not excite the vibration field to any significant extent.

The present invention can control noise either globally or locally depending on the operating parameters of the MRI system. Global control minimizes noise throughout the MRI system, thus the use of the term "global." In local control, noise is minimized at the feedback sensors only. Local control generally results in spherical "zones of silence" centered around each feedback sensor and having a diameter which is a fraction of the acoustic wavelength of the MRI noise. Whether global or local control is achieved depends on the frequencies of the MRI noise and the modal complexity of the primary vibration and acoustic fields of the MRI system being used. Global control can be achieved when the MRI system is being excited at resonance, that is when the frequencies of the MRI noise closely match natural frequencies of the MRI system. However, such resonance conditions produce the highest starting noise levels. Global control is also possible when cancellation is performed at or near the primary source, such as when using modal actuation with distributed actuators. Local control is usually the only possible form of control in non-resonant environments, at off-resonance conditions, and when the secondary field actuators are in the far field of the primary source.

As the MRI noise frequency increases, active noise control becomes more difficult because the acoustic wavelength and thus the "zones of silence" become smaller. At frequencies above about 1 kilohertz, the effectiveness of the active noise control decreases rapidly. As mentioned above, the extent and magnitude of the attenuation varies depending on what modes are excited inside the MRI system and at what frequency. Slight changes in the frequency spectrum of the MRI noise will greatly affect the performance of the active noise control system.

The foregoing has described active control of noise and vibration in an MRI system. Noise and/or vibrations are cancelled by an out-of-phase field generated by vibrational inputs. The system provides efficient noise reduction with a minimum of image distortion.

While specific embodiments of the present invention have been described, it will be apparent to those skilled in the art that various modifications thereto can be made without departing from the spirit and scope of the invention as defined in the appended claims.

What is claimed is:

1. In a magnetic resonance imaging (MRI) device for imaging a subject, and having a cylindrical structure including a magnet, a radio frequency (RF) coil, gradient coils, a pulse signal generator, and system electronics which generate RF pulse signals applied to said RF coil, and gradient pulse signals to energize said gradient coils and thereby create structure-borne primary noise from in-plane structural vibration of said cylindrical structure, an improved MRI apparatus comprising:

means for inducing structural vibrations fixedly mounted on said noise and vibration producing structure to shake said structure and to effect a secondary noise field therefrom for canceling said primary noise to control vibrations in said MRI device to maintain image quality;

means for sensing noise generated by said device, said means for sensing noise producing an error signal corresponding to the level of noise sensed;

means for generating a reference signal representative of said primary noise; and a controller having an input connected to said means for sensing noise, another input connected to said means for generating a reference signal, and an output connected to said means for inducing vibrations, said controller being responsive to said error signal and said reference signal to determine a control signal which is sent to said means for inducing vibrations in said structure, said control signal causing said means for inducing vibrations to vibrate and generate said secondary noise field.

2. The apparatus of claim 1 further comprising a noise canceling member attached to said structure, said noise canceling member supporting said means for inducing vibrations and being vibrated by said means for inducing vibrations to generate said secondary noise field from said structure, and wherein said noise canceling member is resiliently mounted to said structure to decouple vibration of said member from said structure.

3. The apparatus of claim 1 wherein said means for inducing vibrations comprises at least one actuator made of a piezoceramic material.

4. The apparatus of claim 1 wherein said means for generating a reference signal derives said reference signal from said pulse signal generator.

5. The apparatus of claim 1 wherein said means for generating a reference signal is a microphone positioned to detect said primary noise generated by said magnetic resonance imaging device.

6. The apparatus of claim 1 further comprising means for sensing vibrations generated by said structure, said means for sensing vibrations producing a second error signal corresponding to the level of vibrations sensed, and said controller having another input connected to said means for sensing vibrations, said controller being responsive to both of said error signals and said reference signal to determine said control signal which is sent to said means for inducing vibrations with said reference signal not containing crosstalk from said secondary noise field.

7. The apparatus of claim 6 further comprising means for feeding an effort signal proportional to said control signal to said controller.

8. An apparatus for minimizing primary noise generated by a magnetic resonance imaging device having a magnet, a radio frequency coil, gradient coils and a pulse signal generator, said apparatus comprising:

at least one noise canceling member resiliently attached to said device to effect a secondary noise field therefrom for canceling said primary noise, with vibration of said member being decoupled from said device;

a first means for inducing vibrations coupled to said noise canceling member;

a second means for inducing vibrations coupled to said device for vibrating said device;

means for sensing noise generated by said device, said means for sensing noise producing a first error signal corresponding to the level of noise sensed;

means for sensing vibrations generated by said device and being attached thereto, said means for sensing vibrations producing a second error signal corresponding to the level of vibrations sensed in said device;

means for generating a reference signal representative of said primary noise;

a first controller having an input connected to said means for sensing noise, another input connected to said means for generating a reference signal, and an output connected to said first means for inducing vibrations, said first controller being responsive to said first error signal to determine a control signal which is sent to said first means for inducing vibrations, said first control signal causing said first means for inducing vibrations to vibrate and generate said secondary noise field; and a second controller having an input connected to said means for sensing vibrations, another input connected to said means for generating a reference signal, and an output connected to said second means for inducing vibrations, said second controller being responsive to said second error signal to determine a second control signal which is sent to said second means for inducing vibrations, said second control signal causing said second means for inducing vibrations to vibrate and generate a vibration field in said device for canceling said vibrations sensed, with said second controller being configured to activate before said first controller.

9. The apparatus of claim 8 wherein said first and second means for inducing vibrations each comprise at least one actuator made of a piezoceramic material.

10. The apparatus of claim 8 wherein said second means for inducing vibrations is directly mounted to said gradient coils.

11. The apparatus of claim 8 wherein said second means for inducing vibrations is directly mounted to said radio frequency coil.

12. The apparatus of claim 8 wherein said reference signal generating means derives said reference signal from said pulse signal generator, and said first and second controllers are both additionally responsive to gradient pulse signals generated by said pulse signal generator to determine said first and second control signals, respectively.

13. The apparatus of claim 8 wherein said reference signal generating means derives said reference signal from said pulse signal generator, and said first and second controllers are both additionally responsive to radio frequency pulse signals generated by said pulse signal generator to determine said first and second control signals, respectively.

14. The apparatus of claim 8 wherein said means for generating a reference signal is a microphone positioned to detect said primary noise generated by said magnetic resonance imaging device, said first and second controllers each having an additional input connected to said microphone so as to be additionally responsive to signals generated by said microphone to determine said first and second control signals, respectively.

15. In a magnetic resonance imaging (MRI) device for imaging a subject, and having a cylindrical structure including a magnet, a radio frequency (RF) coil, gradient coils, a pulse signal generator, and system electronics which generate RF pulse signals applied to said RF coil, and gradient pulse signals to energize said gradient coils and thereby create structure-borne primary noise from in-plane structural vibration of said cylindrical structure, an improved MRI apparatus comprising:

means for inducing structural vibrations fixedly mounted on said noise and vibration producing structure to shake said structure and to effect a secondary noise field therefrom for canceling said primary noise to control vibrations in said MRI device to maintain image quality;

means for sensing vibrations generated by said device and being attached thereto, said means for sensing vibrations producing an error signal corresponding to the level of vibrations sensed in said device;

means for generating a reference signal representative of said primary noise; and a controller having an input connected to said means for sensing vibrations, another input connected to said means for generating a reference signal, and an output connected to said means for inducing vibrations, said controller being responsive to said error signal to determine a control signal which is sent to said means for inducing vibrations, said control signal causing said means for inducing vibrations to vibrate and generate a vibration field in said cylindrical structure for canceling said vibrations sensed to reduce said primary noise.

16. The apparatus of claim 15 wherein said reference signal generating means derives said reference signal from said pulse signal generator, and said controller is additionally responsive to said gradient pulse signals generated by said pulse signal generator to determine said control signal.

17. The apparatus of claim 15 wherein said reference signal generating means derives said reference signal from said pulse signal generator, and said controller is additionally responsive to said RF pulse signals generated by said pulse signal generator to determine said control signal.

18. The apparatus of claim 15 wherein said means for generating a reference signal is a microphone positioned to detect said primary noise generated by said magnetic resonance imaging device, said controller having an additional input connected to said microphone so as to be additionally responsive to signals generated by said microphone to determine said control signal.

19. The apparatus of claim 15 wherein said means for inducing vibrations is directly mounted to said gradient coils.

20. The apparatus of claim 15 wherein said means for inducing vibrations is directly mounted to said radio frequency coil.

* * * * *